US00PP25238P2

(12) United States Plant Patent
Beekenkamp

(10) Patent No.: US PP25,238 P2
(45) Date of Patent: Jan. 20, 2015

(54) *BEGONIA* PLANT NAMED 'BKPBEELM'

(50) Latin Name: *Begonia hiemalis*
Varietal Denomination: BKPBEELM

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 114 days.

(21) Appl. No.: 13/815,614

(22) Filed: Mar. 11, 2013

(51) Int. Cl.
*A01H 5/00* (2006.01)

(52) U.S. Cl.
USPC ..... Plt./346

(58) Field of Classification Search
USPC ..... Plt./346
See application file for complete search history.

*Primary Examiner* — Annette Para
(74) *Attorney, Agent, or Firm* — C. A. Whealy

(57) ABSTRACT

A new and distinct cultivar of *Begonia* plant named 'BKPBEELM', characterized by its upright, somewhat outwardly spreading and mounded plant habit; freely basal branching habit; dark green-colored leaves; uniform and freely flowering habit; and double and single flowers that are light yellow in color.

2 Drawing Sheets

Botanical designation: *Begonia hiemalis*.
Cultivar denomination: 'BKPBEELM'.

BACKGROUND OF THE INVENTION

The present invention relates to a new and distinct cultivar of *Begonia* plant, botanically known as *Begonia hiemalis*, commercially referred to as a Elatior *Begonia* and hereinafter referred to by the name 'BKPBEELM'.

The new *Begonia* plant is a product of a planned breeding program conducted by the Inventor in Maasdijk, The Netherlands. The objective of the breeding program was to develop new freely branching and freely flowering *Begonia* plants with attractive flower color.

The new *Begonia* plant is a naturally-occurring branch mutation of a proprietary selection of *Begonia hiemalis* identified as code number 6500676, not patented. The new *Begonia* plant was discovered and selected by the Inventor on a single flowering plant from within a population of plants of the parent selection in a controlled greenhouse environment in Maasdijk, The Netherlands in September, 2010.

Asexual reproduction of the new *Begonia* plant by tip cuttings in a controlled greenhouse environment in Maasdijk, The Netherlands since December, 2010 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEELM'. These characteristics in combination distinguish 'BKPBEELM' as a new and distinct *Begonia* plant:

1. Upright, somewhat outwardly spreading and mounded plant habit.
2. Freely basal branching habit.
3. Dark green-colored leaves.
4. Uniform and freely flowering habit.
5. Double and single flowers that are light yellow in color.

Plants of the new *Begonia* can be compared to plants of the mutation parent selection. Plants of the new *Begonia* differ from plants of the mutation parent selection primarily in flower color as plants of the mutation parent selection have orange-colored flowers.

Plants of the new *Begonia* can be compared to plants of the *Begonia* 'Daisy Franje', disclosed in U.S. Plant Pat. No. 10,804. In side-by-side comparisons conducted in Maasdijk, The Netherlands, plants of the new *Begonia* differed from plants of 'Daisy Franje' in the following characteristics:

1. Plants of the new *Begonia* had darker green-colored leaves than plants of 'Daisy Franje'.
2. Tepal margins of plants of the new *Begonia* were entire whereas tepal margins of plants of 'Daisy Franje' were incised giving a fringed appearance.
3. Plants of the new *Begonia* and 'Daisy Franje' differed slightly in flower color.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEELM' grown in a container.

The photograph on the second sheet are close up views of typical flower buds, flowers and leaves of 'BKPBEELM'.

DETAILED BOTANICAL DESCRIPTIONS

Plants used for the aforementioned photographs and following observations and measurements were grown in 12-cm containers during the winter in a glass-covered greenhouse in Maasdijk, The Netherlands. During the production of the plants, day temperatures ranged from 19° to 20° C., night temperatures ranged from 18° to 19° C. and light levels averaged 6,000 lux. Plants were eleven weeks old when the photographs and the description were taken. In the following description, color references are made to The Royal Horticultural Society Colour Chart, 2007 Edition, except where general terms of ordinary dictionary significance are used.

Botanical classification: *Begonia hiemalis* 'BKPBEELM'.

Parentage: Naturally-occurring branch mutation of a proprietary selection of *Begonia hiemalis* identified as code number 6500676, not patented.

Propagation:

*Type*.—By tip cuttings.

*Time to initiate roots*.—About 20 days at temperatures about 25° C.

*Time to produce a rooted young plant*.—About 35 to 36 days at temperatures about 21° C. to 23° C.

*Root description*.—Fine, fibrous; light brown in color; plants of the new *Begonia* have not been observed to form tubers.

*Rooting habit*.—Moderate branching; medium density.

Plant description:

*Plant and growth habit*.—Upright, somewhat outwardly spreading and mounded plant habit; plant shape roughly globular to obovate; freely basal branching with about six basal branches per plant; moderately vigorous growth habit.

*Plant height*.—About 24 cm.

*Plant width*.—About 26 cm.

*Lateral branch description*.—Length: About 9.9 cm. Diameter: About 7 mm. Internode length: About 2.2 cm. Texture: Smooth, glabrous. Aspect: Upright to about 30° from the vertical. Color, developing: Close to 146B to 146C. Color, fully developed: Close to 146A and 152A.

*Leaf description*.—Arrangement: Alternate, simple. Length: About 10.7 cm. Width: About 8.3 cm. Shape: Roughly ovate, unequal. Apex: Broadly acute. Base: Oblique to hastate. Margin: Bi-serrate to bi-crenate. Texture, upper surface: Smooth, glabrous; velvety. Texture, lower surface: Sparsely pubescent along margins and main veins. Venation pattern: Palmate. Color: Developing leaves, upper surface: Darker than between 147A and N189A. Developing leaves, lower surface: Close to 176B. Fully expanded leaves, upper surface: Darker than between 147A and N189A; venation, close to 143A. Fully expanded leaves, lower surface: Close to 147B tinged with close to 182B; venation, close to 146A. Petioles: Length: About 5.4 cm. Diameter: About 5 mm. Texture, upper and lower surfaces: Pubescent. Color, upper surface: Close to 146A to 146B; towards the leaf, close to 183B. Color, lower surface: Close to 146B; towards the leaf, close to 183B.

Flower description:

*Flowering habit*.—Female flowers, single; male flowers, double; flowers arranged in axillary compound cymes; freely flowering habit with two female flowers and about ten male flowers per cyme and about 360 male and female flowers developing per plant; flowers face upright to outwardly.

*Fragrance*.—None detected.

*Natural flowering season*.—Plants begin flowering about 65 days after planting; long flowering period, plants flower freely and continuously from spring into the autumn in The Netherlands.

*Flower longevity*.—Individual flowers last about ten days on the plant; flowers not persistent.

*Inflorescence height*.—About 14.6 cm.

*Inflorescence diameter*.—About 14.5 cm.

*Female flower diameter*.—About 4.9 cm.

*Female flower height*.—About 2.6 cm.

*Male flower diameter*.—About 5.1 cm.

*Male flower height*.—About 1.9 cm.

*Flower buds*.—Length: About 1.7 cm. Diameter: About 6 mm to 18 mm. Shape: Orbicular, flattened. Color: Close to 145D; towards the margins, close to 150D.

*Tepals, female flowers*.—Quantity per flower and arrangement: About five in a single whorl. Length: About 3.1 cm. Width: About 3 cm. Shape: Broadly obovate to nearly orbicular. Apex: Rounded. Margin: Entire. Texture, upper and lower surfaces: Smooth, glabrous; slightly velvety. Color: When opening, upper surface: Close to 1C to 1D and 3C. When opening, lower surface: Close to 150D; towards the base, close to 150C. Fully opened, upper surface: Close to 8C; towards the margins, close to 8D; color does not fade with development. Fully opened, lower surface: Close to 8D; color does not fade with development.

*Tepals, male flowers*.—Quantity per flower and arrangement: Two, opposite. Length: About 2.9 cm. Width: About 3 cm. Shape: Orbicular to reniform. Apex: Rounded. Margin: Entire. Texture, upper and lower surfaces: Smooth, glabrous; slightly velvety. Color: When opening, upper surface: Close to 1C to 1D and 3C. When opening, lower surface: Close to 150D; towards the base, close to 150C. Fully opened, upper surface: Close to 4C; towards the margins, close to 4D; color does not fade with development. Fully opened, lower surface: Close to 1C to 1D; towards the margins, close to 2D; color does not fade with development.

*Tepaloids, present on male flowers only*.—Quantity per flower and arrangement: About 22 in multiple whorls. Length: About 1.9 cm. Width: About 1.6 cm. Shape: Obovate. Apex: Rounded. Margin: Entire. Texture, upper and lower surfaces: Smooth, glabrous; slightly velvety. Color: When opening, upper surface: Close to 4B to 4C. When opening, lower surface: Close to 4D. Fully opened, upper surface: Close to 4C; color does not fade with development. Fully opened, lower surface: Close to 4D; color does not fade with development.

*Peduncles*.—Length: About 12.2 cm. Diameter: About 4.5 mm to 5 mm. Angle: About 30° from vertical. Strength: Flexible, bending with the weight of the flowers. Texture: Smooth, glabrous. Color: Close to 146A.

*Pedicels*.—Length, female flowers: About 3.3 cm. Diameter, female flowers: About 2 mm. Length, male flowers: About 1.8 cm. Diameter, male flowers: About 2 mm. Angle: About 40° from the peduncle axis. Strength: Flexible, bending with the weight of the flowers. Texture: Densely pubescent. Color: Close to 144A to 144B.

*Reproductive organs*.—Androecium: Not observed on plants of the new *Begonia*. Gynoecium, present only on female flowers: Quantity of pistils per flower: Five. Pistil length: About 9 mm. Style length: About 4 mm. Style color: Close to 154A to 154B. Stigma color: Close to 14A to 14B. Ovary color: Close to 145A to 145B.

*Seeds and fruits*.—Seed and fruit development production has not been observed on plants of the new *Begonia*.

Disease & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'BKPBEELM' as illustrated and described.

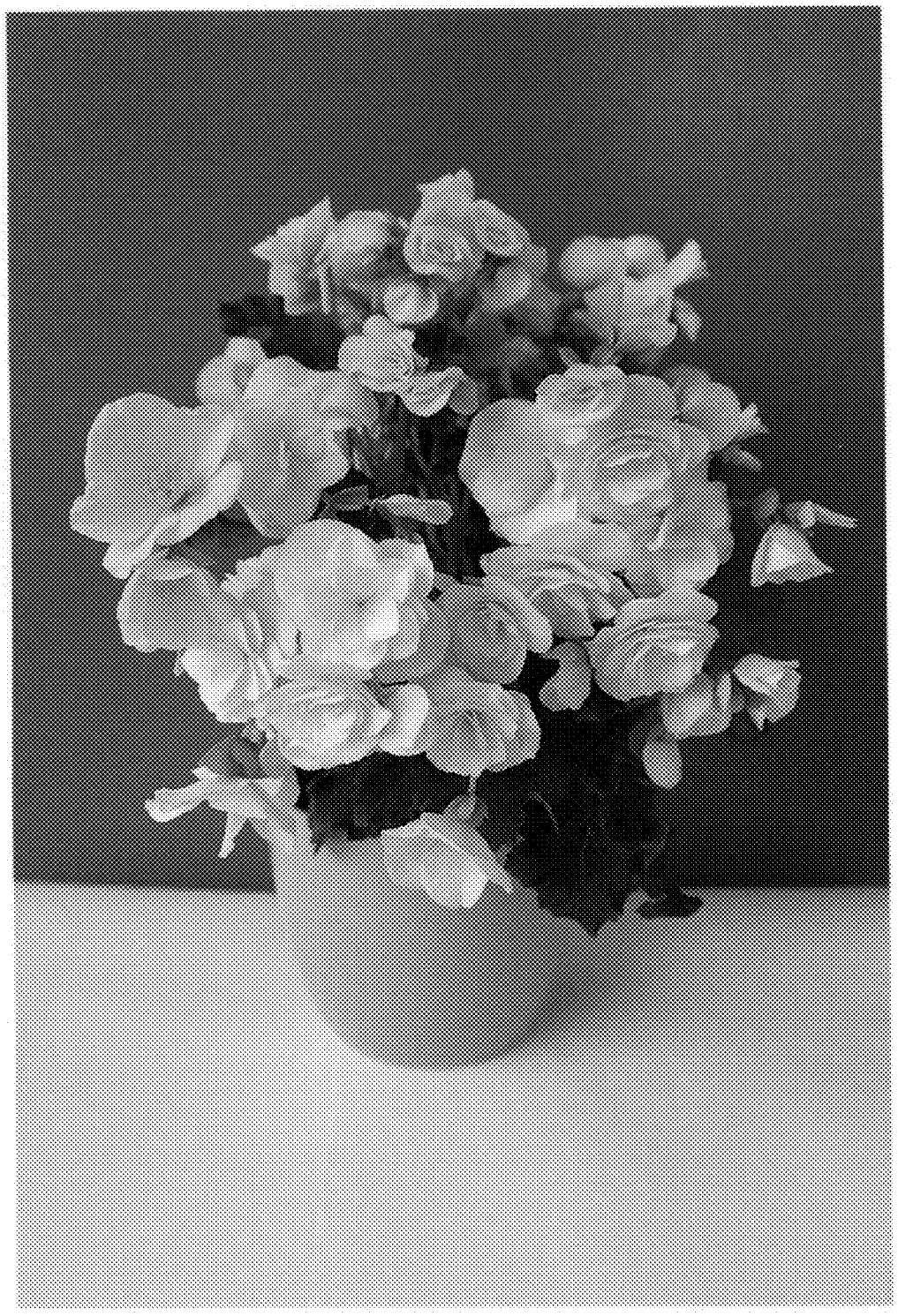

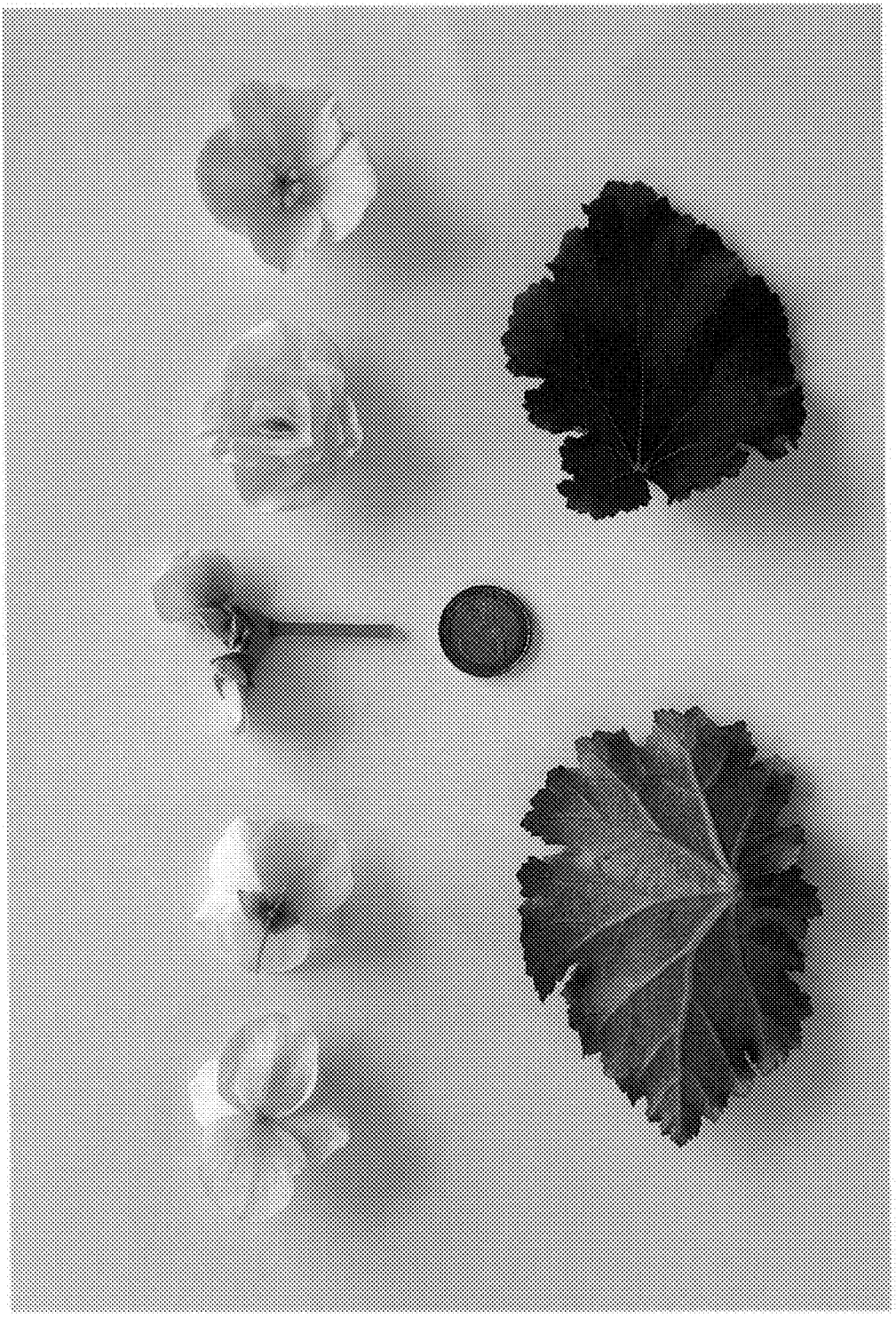

* * * * *